United States Patent
Hurley

(10) Patent No.: US 11,560,354 B2
(45) Date of Patent: *Jan. 24, 2023

(54) COMPOSITIONS COMPRISING (R)-2-AMINO-3-PHENYLPROPYL CARBAMATE AND USES THEREOF

(71) Applicants: AXSOME MALTA LTD., Qormi (MT); SK Biopharmaceuticals Co., Ltd., Seongnam-si (KR)

(72) Inventor: Fionn Hurley, Baldoyle (IE)

(73) Assignees: Axsome Malta Ltd., Qormi (MT); SK Biopharmaceuticals Co., Ltd., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/091,222

(22) Filed: Nov. 6, 2020

(65) Prior Publication Data

US 2021/0053912 A1  Feb. 25, 2021

Related U.S. Application Data

(63) Continuation of application No. 16/331,069, filed as application No. PCT/US2017/050233 on Sep. 6, 2017, now Pat. No. 10,829,443.

(60) Provisional application No. 62/383,822, filed on Sep. 6, 2016.

(51) Int. Cl.
| | |
|---|---|
| *C07C 271/12* | (2006.01) |
| *A61K 45/06* | (2006.01) |
| *A61P 3/04* | (2006.01) |
| *A61P 25/24* | (2006.01) |
| *C07C 269/08* | (2006.01) |

(52) U.S. Cl.
CPC ............ *C07C 271/12* (2013.01); *A61K 45/06* (2013.01); *A61P 3/04* (2018.01); *A61P 25/24* (2018.01); *C07B 2200/13* (2013.01); *C07C 269/08* (2013.01)

(58) Field of Classification Search
CPC .................................................... C07C 271/12
See application file for complete search history.

(56) References Cited

U.S. PATENT DOCUMENTS

| | | | | |
|---|---|---|---|---|
| 5,955,499 | A | * | 9/1999 | Choi ................. A61P 25/28 560/163 |
| 6,350,596 | B2 | | 2/2002 | Iomantas et al. |
| 9,403,761 | B2 | | 8/2016 | Kang et al. |
| 9,604,917 | B2 | | 3/2017 | Ahnaou et al. |
| 9,649,291 | B2 | | 5/2017 | Khayrallah et al. |
| 10,829,443 | B2 | * | 11/2020 | Nelson ................. C07C 271/12 |
| 2005/0080268 | A1 | | 4/2005 | Choi et al. |
| 2010/0331332 | A1 | | 12/2010 | Lee et al. |
| 2014/0350098 | A1 | | 11/2014 | Ahnaou et al. |
| 2015/0025136 | A1 | | 1/2015 | Khayrallah et al. |
| 2015/0246874 | A1 | | 9/2015 | Kang et al. |
| 2016/0081970 | A1 | | 3/2016 | Khayrallah et al. |

FOREIGN PATENT DOCUMENTS

| | | |
|---|---|---|
| CN | 1135209 A | 11/1996 |
| JP | H09503231 A | 3/1997 |
| JP | 2007508293 A | 4/2007 |
| JP | 2008546778 A | 12/2008 |
| JP | 2016532679 A | 10/2016 |
| JP | 2017512211 A | 5/2017 |
| JP | 2019512009 A | 5/2019 |
| KR | 100197892 B1 | 6/1999 |
| KR | 20080035565 A | 4/2008 |
| KR | 20160032127 A | 3/2016 |
| KR | 20180032127 A | 3/2018 |
| WO | 9607637 A1 | 3/1996 |
| WO | 2005033064 A1 | 4/2005 |
| WO | 2007001841 A1 | 1/2007 |
| WO | 2017140778 A1 | 8/2017 |

OTHER PUBLICATIONS

"Extended European Search Report corresponding to European Application No. 17849432.4 dated Apr. 9, 2020".
"International Preliminary Report on Patentability corresponding to International Application No. PCT/US2017/050233 dated Mar. 21, 2019".
"International Search Report and Written Opinion corresponding to International Application No. PCT/US2017/050233 dated Nov. 13, 2017".
"International Search Report corresponding to Singapore Application No. 11201901998W dated May 2, 2020".
"Written Opinion corresponding to Singapore Application No. 11201901998W dated May 6, 2020".
Phenprobamate, Wikipedia, https://en.wikipedia.org/wiki/Phenprobamate, last edited Apr. 2, 2016, accessed Sep. 24, 2019.
"Office Action corresponding to Chinese Application No. 2017800651926 dated Jul. 5, 2021".
Fang, Lao , et al., "Inventiveness of Crystal Forms of a Drug, from the view of Patent Invalidation or Administrative Litigation Cases", China Invention & Patent 2:110-116 (Feb. 16, 2016).
"Office Action corresponding to Chinese Application No. 201780065192.6 dated Dec. 6, 2021".
"Office Action corresponding to Indonesian Application No. PID201902732 dated Dec. 6, 2021".
"Office Action corresponding to Japanese Application No. 2019-512895 dated Dec. 12, 2021".

(Continued)

*Primary Examiner* — Matthew P Coughlin

(74) *Attorney, Agent, or Firm* — Myers Bigel, P.A.

(57) ABSTRACT

The present invention relates to a newly identified solvate form of (R)-2-amino-3-phenylpropyl carbamate (APC) hydrochloride, a method of preparing APC hydrochloride, and methods of using the same to treat disorders. The invention further relates to methods of producing APC hydrochloride with increased purity.

8 Claims, 5 Drawing Sheets

(56) References Cited

OTHER PUBLICATIONS

Ashizawa, Kazuhide, et al., "Science of Polymorphism and crystallization of the pharmaceutical drugs: Trends in development, manufacturing and regulations", Sep. 20, 2002, 273-278.
"Office Action corresponding to Indonesian Application No. PID201902732 dated Jul. 27, 2021".
"Examination Report corresponding to European Application No. 17849432.4 dated May 11, 2021".
"Office Action corresponding to Indonesian Application No. PID201902732 dated Mar. 18, 2021".
"Office Action corresponding to Indian Application No. 201917009658 dated Nov. 24, 2020".
"Office Action corresponding to Japanese Application No. 2019-512895 dated Jun. 28, 2021".
"Written Opinion corresponding to Singapore Application No. 11201901998W dated Jun. 29, 2021".
"Office Action corresponding to Chinese Application No. 2017800651926 dated Mar. 9, 2022".
"Office Action corresponding to European Application No. 17849432.4 dated Apr. 8, 2022".
"Office Action corresponding to Philippine Application No. 1-2019-500493 dated Feb. 10, 2022".
"Written Opinion corresponding to Singapore Application No. 11201901998W dated May 16, 2022".
"Office Action corresponding to Japanese Application No. 2019-512895 dated Jun. 27, 2022".
"Office Action corresponding to Korean Application No. 10-2019-7011279 dated Jul. 20, 2022".

* cited by examiner

*ISOLATED FROM 24 HOUR SLURRY IN WATER:
ACN (5:95 V:V), CONCENTRATION ~98 mg/ml

**ISOLATED FROM 24 HOUR SLURRY IN WATER:
ACN (5:95 V:V), CONCENTRATION ~51 mg/ml

COMPOSITIONS COMPRISING (R)-2-AMINO-3-PHENYLPROPYL CARBAMATE AND USES THEREOF

STATEMENT OF PRIORITY

This application is a continuation of U.S. patent application Ser. No. 16/331,069, filed Mar. 6, 2019, now U.S. Pat. No. 10,829,443, which is a 35 U.S.C. § 371 national phase application of PCT Application PCT/US2017/050233 filed Sep. 6, 2017, which claims the benefit, under 35 U.S.C. § 119(e), of U.S. Provisional Application No. 62/383,822, filed Sep. 6, 2016; the entire contents of each of which are incorporated by reference herein in its entirety.

FIELD OF THE INVENTION

The present invention relates to a newly identified solvate form of (R)-2-amino-3-phenylpropyl carbamate (APC) hydrochloride, a method of preparing APC hydrochloride, and methods of using the same to treat disorders. The invention further relates to methods of producing APC hydrochloride with increased purity.

BACKGROUND OF THE INVENTION

APC is a phenylalanine analog that has been demonstrated to be useful in the treatment of a variety of disorders, including excessive daytime sleepiness, cataplexy, narcolepsy, fatigue, depression, bipolar disorder, fibromyalgia, and others. See, for example, U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414. Methods for producing APC (which also has other names) and related compounds can be found in U.S. Pat. Nos. 5,955,499; 5,705,640; 6,140,532 and 5,756,817. All of the above patents and applications are hereby incorporated herein by reference in their entireties for all purposes.

The present invention overcomes shortcomings in the art by providing a new solvate form of APC and a method of preparing APC with minimal contaminants.

SUMMARY OF THE INVENTION

The present invention relates to the identification of a novel solvate form of APC which is a hemihydrate form. The invention further relates to a method of preparing APC with minimal contaminants. The invention additionally relates to the use of the new solvate form and/or the APC with increased purity for the treatment of disorders responsive to APC.

Accordingly, the invention relates to a solvate form of APC hydrochloride characterized by a powder x-ray diffraction pattern substantially the same as that shown in FIG. 1 and/or a powder x-ray diffraction pattern having peaks at about 7.0, 13.6, 16.2, 17.4, 17.8, 18.5, 21.0, 21.7, 22.7, 23.0, 24.0, and 27.3±0.2° 2θ.

The invention further relates to a process of preparing a solvate form of APC hydrochloride, comprising slurrying APC hydrochloride in acetonitrile/water (95%/5% v/v) and collecting the solvate by vacuum filtration.

The invention further relates to a composition comprising APC, wherein less than about 10% of the APC in the composition is the solvate form of the invention.

The invention also relates to a composition comprising APC, wherein at least about 30% of the APC in the composition is the solvate form of the invention.

The invention additionally relates to a method of treating a disorder amenable to treatment with APC, e.g., narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity in a subject in need thereof, or promoting smoking cessation in a subject in need thereof, comprising administering to the subject a dosage form comprising the solvate form of the invention.

The invention also relates to a method of preparing APC hydrochloride while minimizing contamination with 2-chloropropane, the method comprising crystallizing APC in the presence of aqueous HCl, thereby producing crystals of APC hydrochloride.

The invention further relates to a composition comprising APC with increased purity as prepared by the method of the invention.

The invention additionally relates to a method of treating a disorder amenable to treatment with APC, e.g., narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity in a subject in need thereof, or promoting smoking cessation in a subject in need thereof, comprising administering to the subject a dosage form comprising APC with increased purity as prepared by the method of the invention.

The present invention is explained in greater detail in the drawings herein and the specification set forth below.

DETAILED DESCRIPTION OF THE INVENTION

Figure 1:
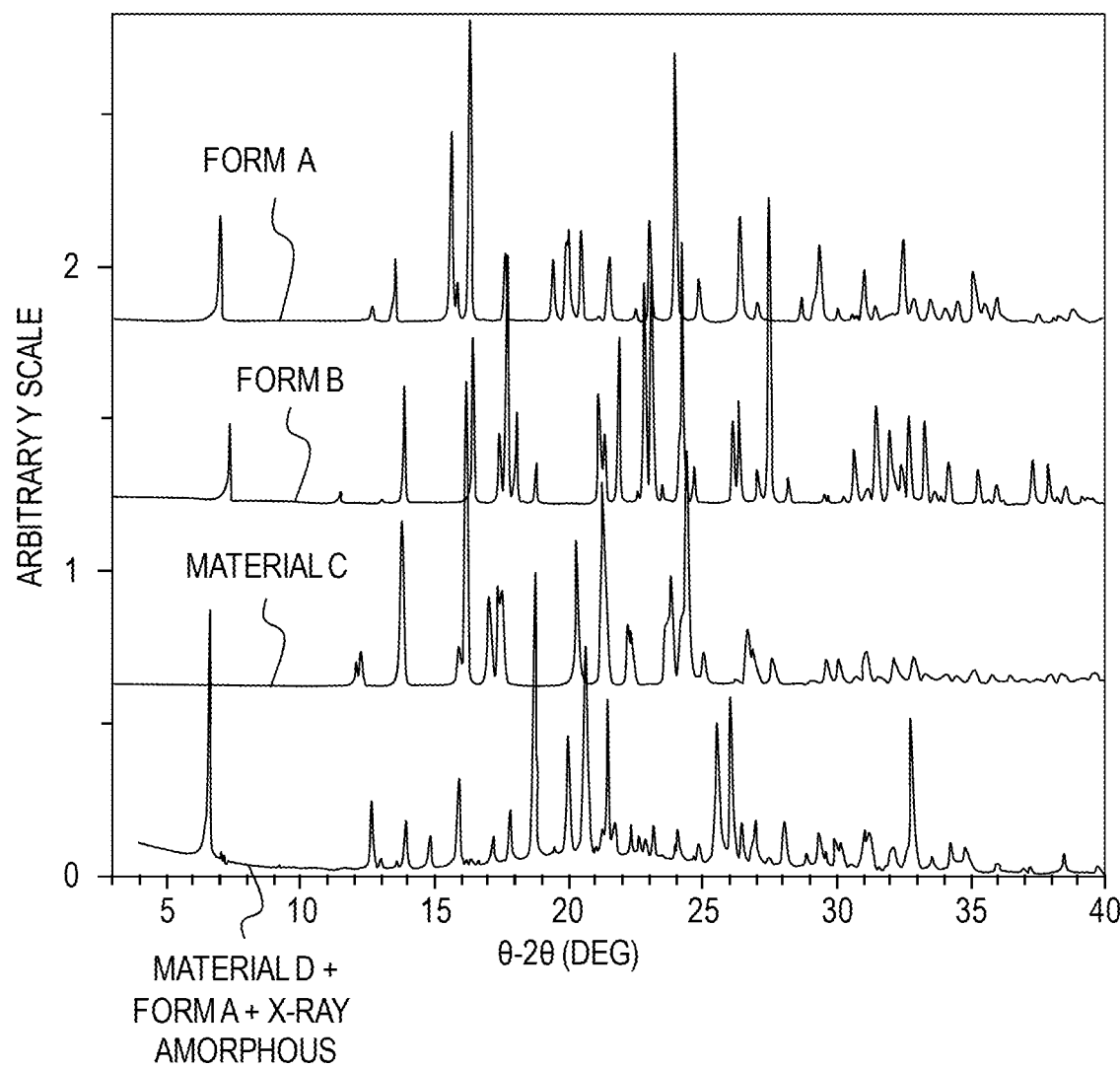
FIG. 1 shows the X-ray pattern diffraction (XRPD) of crystalline forms of APC.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety for all purposes.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 10%, 5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "therapeutically effective amount" or "effective amount," as used herein, refers to the amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

A "disorder amenable to treatment with APC" refers to any disorder in which administration of APC to a subject results in the treatment of one or more symptoms of the disorder in the subject. Examples of such disorders include, without limitation, narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* $21^{st}$ ed. 2005).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The present invention relates to the identification and characterization of a new solvate form of APC hydrochloride, called Form B. The solvate form is a hemihydrate form and is the more stable form of the compound at higher humidity levels compared to the anhydrous Form A.

The structure of APC free base is given below as formula I.

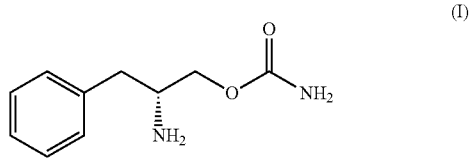 [SMILES: NC(=O)OC[C@H](N)Cc1ccccc1]

Thus, one aspect of the invention relates to a solvate form of APC hydrochloride characterized by a powder x-ray diffraction pattern substantially the same as that shown in FIG. 1 for solvate Form B and/or a powder x-ray diffraction pattern having peaks at about 7.0, 13.6, 16.2, 17.4, 17.8, 18.5, 21.0, 21.7, 22.7, 23.0, 24.0, and 27.3±0.2° 2θ. In some embodiments, the solvate is further characterized by differential scanning calorimetry as having a broad endotherm with onset at 69.1° C. and peak at 71.7° C. and a sharp endotherm with onset at 182.5° C. and peak at 183.6° C. In some embodiments, the solvate is further characterized by having a solubility in buffer solution of about 700-750 mg/ml at pH 1-6.5. In certain embodiments, the solvate form is a hemihydrate.

In some embodiments, the solvate form is further characterized as being produced by slurrying APC in acetonitrile/water (95%/5% v/v).

As used herein, the term "hemihydrate," refers to a hydrate in which one molecule of water is associated with two molecules of APC.

As used herein, the term "crystalline" refers to a material that contains a specific compound, which may be hydrated and/or solvated, and has sufficient crystal content to exhibit a discernible diffraction pattern by XRPD or other diffraction techniques.

The solvate form may be prepared by a method comprising slurrying APC hydrochloride in a suitable solvent system (e.g., acetonitrile/water (95%/5% v/v)) and collecting the solvate crystals using a suitable technique, e.g., vacuum filtration. In some embodiments, the process is carried out at about room temperature, e.g., about 20° C. to about 28° C. and in about 5-15 (e.g., 10) volumes of solvent. In some embodiments, the slurrying step is carried out for a sufficient length of time for the solvate to form, e.g., at least about 10 hours, e.g., at least about 10, 15, 20, 25, 50, 75, or 100 hours or more.

In some embodiments, the process is carried out at a temperature of about 20° C. and in about 5 volumes of solvent. In some embodiments, the slurrying step is carried out for a sufficient length of time for the solvate to form, e.g., about 1-2 hours.

The wet Form B prepared by the methods described herein may be dried by any method suitable for maintaining Form B and limiting dehydration to Form A. In some embodiments, the drying is carried out at a temperature of about 20° C. to about 25° C. In some embodiments, the drying is carried out at reduced pressure, e.g., about 600-950 mbar e.g., about 700-750 mbar. In some embodiments, the drying is carried out for a suitable length of time to achieve complete dryness, e.g., about 4-40 hours, e.g., about 10-24 hours. In some embodiments, the drying is carried out at high humidity, e.g., about 80-100% relative humidity.

Another aspect of the invention relates to a composition, e.g., a dosage form, comprising APC, wherein less than about 10% of the APC in the composition is solvate Form B. In some embodiments, less than about 9%, 8%, 7%, 6%, 5%, 4%, 3%, 2%, or 1% of the APC is in solvate Form B. In some embodiments, the dosage form is an oral dosage form, e.g., a tablet or a capsule, including, e.g., an immediate release dosage form.

A further aspect of the invention relates to a composition, e.g., a dosage form, comprising APC, wherein at least about 30% of the APC in the composition is solvate Form B, e.g., about 30% to about 99% or more. In some embodiments, at least about 40%, 50%, 60%, 70%, 80%, or 90% of the APC is solvate Form B. In some embodiments, the dosage form is an oral dosage form, e.g., a tablet or a capsule, including, e.g., an immediate release dosage form.

In some embodiments, the dosage form is an immediate release dosage form that releases at least 85%, e.g., at least 85%, 86%, 87%, 88%, 89%, 90%, 91%, 92%, 93%, 94%, 95%, 96%, 97%, 98%, or 99%, of the APC HCl contained therein within a period of less than 15 minutes after administration of the tablet to a subject. Such immediate release dosage forms are disclosed, for example, U.S. Provisional Application No. 62/383,818, incorporated herein by reference in its entirety.

Formulations of APC, including immediate release formulations, may be processed into unit dosage forms suitable for oral administration, such as for example, filled capsules, compressed tablets or caplets, or other dosage form suitable for oral administration using conventional techniques. Immediate release dosage forms prepared as described may be adapted for oral administration, so as to attain and maintain a therapeutic level of APC over a preselected interval. In certain embodiments, an immediate release dosage form as described herein may comprise a solid oral dosage form of any desired shape and size including round, oval, oblong cylindrical, or polygonal. In one such embodiment, the surfaces of the immediate release dosage form may be flat, round, concave, or convex.

In particular, when the immediate release formulations are prepared as a tablet, the immediate release tablets contain a relatively large percentage and absolute amount of APC and so are expected to improve patient compliance and convenience by replacing the need to ingest large amounts of liquids or liquid/solid suspensions. One or more immediate release tablets as described herein can be administered, by oral ingestion, e.g., closely spaced, in order to provide a therapeutically effective dose of APC to the subject in a relatively short period of time.

Where desired or necessary, the outer surface of an immediate release dosage form may be coated, e.g., with a color coat or with a moisture barrier layer using materials and methods known in the art.

The dosage form may contain any amount of APC or a pharmaceutically acceptable salt thereof suitable for administration as a unit dosage form. In some embodiments, the dosage form contains about 1 mg to about 1000 mg of the drug or any range or value therein, e.g., about 10 mg to about 500 mg, e.g., about 37.5 mg, about 75 mg, about 150 mg, or about 300 mg.

APC or a pharmaceutically acceptable salt thereof may be obtained or synthesized by methods known in the art and as described herein. Details of reaction schemes for synthesizing APC have been described in U.S. Pat. Nos. 5,705,640; 5,756,817; 5,955,499; and 6,140,532, all incorporated herein by reference in their entirety.

During the development of manufacturing processes for APC, it was found that unacceptable levels of the impurity 2-chloropropane (i.e., isopropyl chloride) could appear during the crystallization of APC hydrochloride. It is desirable to minimize 2-chloropropane as it is a potential genotoxic impurity. Thus, one aspect of the invention relates to an improved method of preparing APC hydrochloride in which contamination with 2-chloropropane is minimized. With this improved method, the level of 2-chloropropane in the final product may be less than about 10 ppm, e.g., less than about 9, 8, 7, 6, 5, 4, 3, 2, or 1 ppm.

Thus, one aspect of the invention relates to a method of preparing APC hydrochloride while minimizing contamination with 2-chloropropane, the method comprising crystallizing APC in the presence of aqueous HCl, thereby producing crystals of APC hydrochloride. The crystallization may be carried out with the free base of APC in a suitable solvent, e.g., isopropanol.

In some embodiments, the aqueous HCl is 37% aqueous HC. In some embodiments, the crystallization is carried out at a temperature of about 15° C. to about 40° C., e.g., about 25° C. to about 35° C., followed by cooling to a temperature of less than 0° C., e.g., about −5° C. to about −25° C., e.g., about −15° C. In some embodiments, the crystals are dried at a temperature less than about 45° C., e.g., less than about 40° C., 35° C., or 30° C. In some embodiments, the crystallization is carried out in the presence of about 1 to about 1.2 molar equivalents (e.g., about 1.05 molar equivalents) of 37% aqueous HCl at a temperature of about 25° C. to about 35° C. followed by a temperature of about −15° C.

Methods are disclosed herein to treat conditions amenable to treatment by APC, by administering an effective amount of one or more dosage forms as described herein. For example, the present dosage forms can be administered to treat a subject in need of treatment for narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity, or to promoting smoking cessation in a subject in need thereof. See, e.g., U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414; each of which is incorporated by reference in its entirety with respect to the disorder to be treated.

The dosage forms disclosed herein can also be provided as a kit comprising, for example, a container comprising a plurality of immediate release tablets or capsules, which tablets or capsules can be individually packaged, as in foil envelopes or in a blister pack. The tablets or capsules can be packaged in many conformations with or without desiccants or other materials to prevent ingress of water. Instruction materials or means, such as printed labeling, can also be included for their administration, e.g., sequentially over a preselected time period and/or at preselected intervals, to yield the desired levels of APC in vivo for preselected periods of time, to treat a preselected condition.

A daily dose of about 1 to about 2000 mg of APC or a pharmaceutically acceptable salt thereof may be administered to accomplish the therapeutic results disclosed herein. For example, a daily dosage of about 10-1000 mg, e.g., about 20-500 mg, in single or divided doses, is administered. In some embodiments, the daily dose may be about 0.01 to about 150 mg/kg body weight, e.g., about 0.2 to about 18 mg/kg body weight.

In one embodiment of the invention, APC is administered to the subject as needed to treat a disorder. The compound can be administered continuously or intermittently. In one embodiment, the compound is administered to the subject more than once a day, e.g., 2, 3, or 4 times per day, or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject. In another embodiment, the compound can be administered to build up to a certain level, then maintained at a constant level and then a tailing dosage.

In one aspect of the invention, APC is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Further agents include, without limitation, stimulants, antipsychotics, anti-depressants, agents for neurological disorders, and chemotherapeutic agents. One therapeutic agent that can be administered during the same period is Xyrem®, sold commercially by Jazz Pharmaceuticals, which is used to treat narcolepsy and cataplexy. See U.S. Pat. Nos. 8,952,062 and 9,050,302.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has a disorder amenable to treatment with APC. In other embodiments, the subject used in the methods of the invention is an animal model of a disorder amenable to treatment with APC.

The subject can be a subject "in need of" the methods of the present invention, e.g., in need of the therapeutic effects of the inventive methods. For example, the subject can be a subject that is experiencing a disorder amenable to treatment with APC, is suspected of having a disorder amenable to treatment with APC, and/or is anticipated to experience a disorder amenable to treatment with APC, and the methods and compositions of the invention are used for therapeutic and/or prophylactic treatment.

The present invention is explained in greater detail in the following non-limiting Examples.

Example 1

Solvate form of (R)-2-amino-3-phenylpropyl carbamate hydrochloride

A polymorph and solvate screen of APC was conducted to evaluate its propensity to exist in various solid forms and determine the stable form of the compound. Four lots of APC were partially characterized. All lots were found to be the same anhydrous, crystalline material, and the material was designated Form A.

The polymorph and solvate screen of APC was conducted using different crystallization techniques to vary conditions of nucleation and growth investigating both thermodynamic and kinetic conditions. Solvent systems with varying chemical properties were used, and selected experiments focused specifically on process solvents. Selected experiments were also conducted via salt formation experiments using the free base and targeting the monohydrochloride salt.

A crystalline hemihydrate form was identified and named Form B. Form B was prepared from a slurry in acetonitrile:water (95%:5% v:v) at room temperature. Form B was also produced from a slurry in p-dioxane:water (95%:5% v:v) at subambient temperature. Form B was also observed as mixtures with Form A or other crystalline materials from various experiments such as evaporations and crash precipitations in ethanol, hexafluoroisopropanol, methanol, and/or water. Partial conversion to Form B was also observed after stressing of Form A at approximately 75% humidity (RH).

Figure 2:
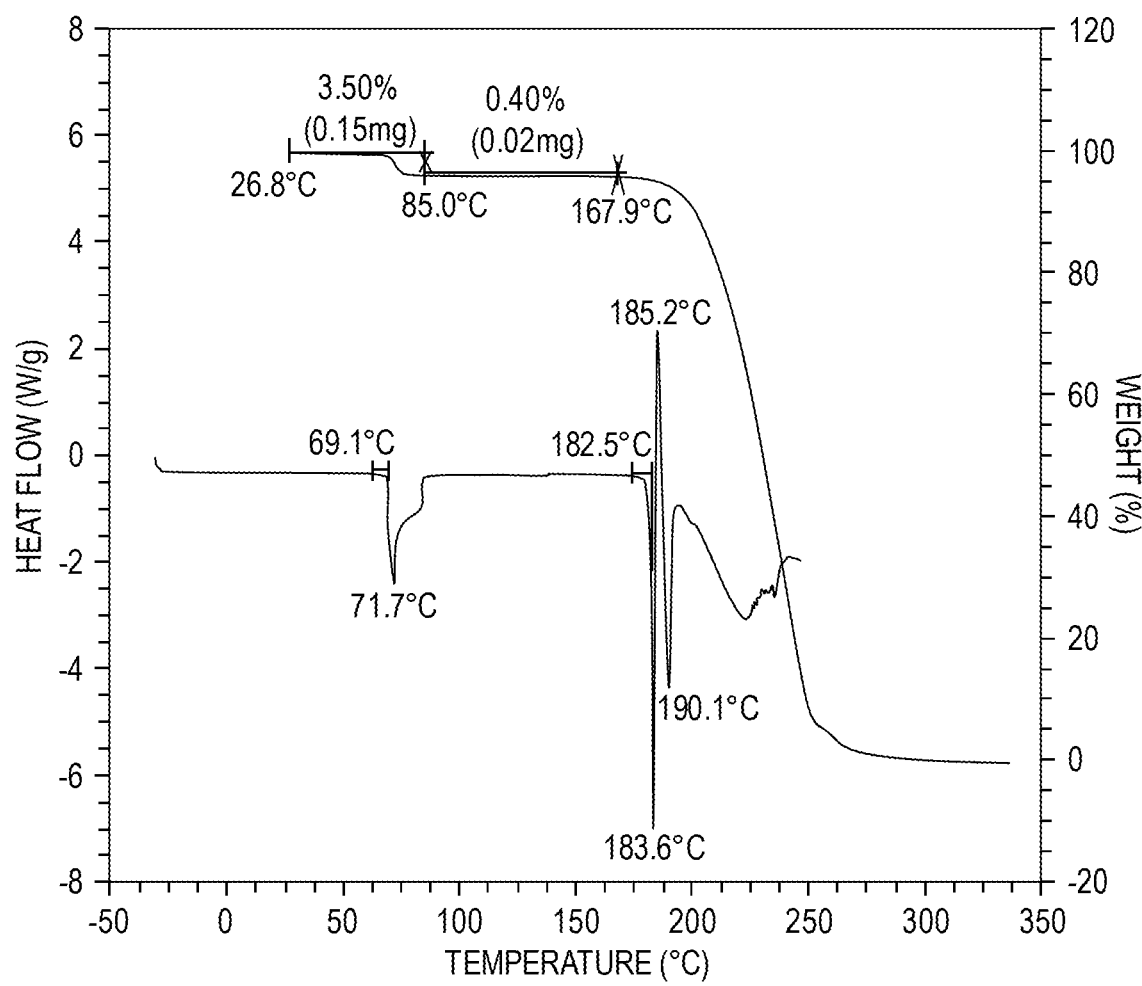
FIG. 2 shows the differential scanning calorimetry (DSC) thermogram of hemihydrate Form B of APC.
Figure 3:
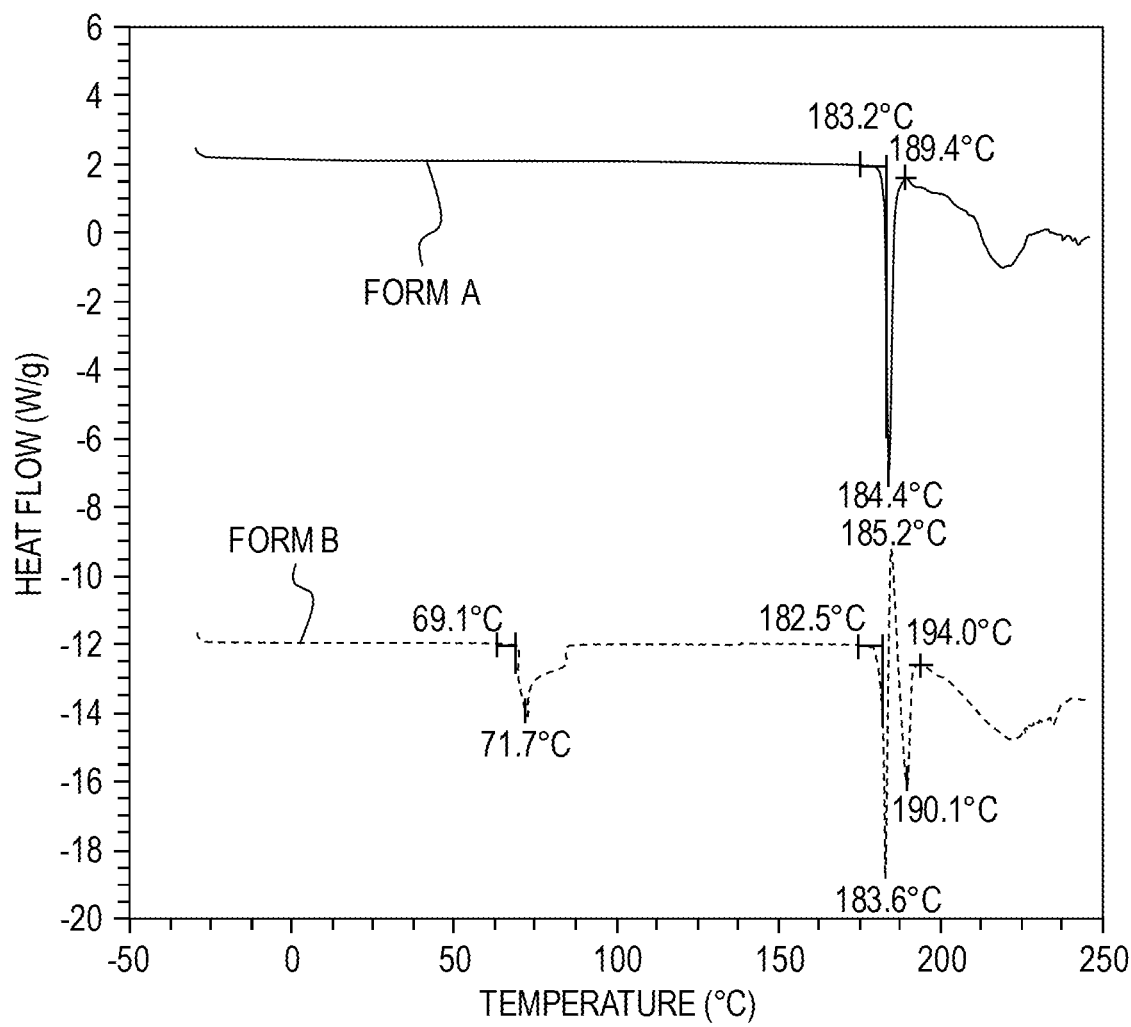
FIG. 3 shows a comparison of the DSC thermograms of Forms A and B of APC.
Figure 4:
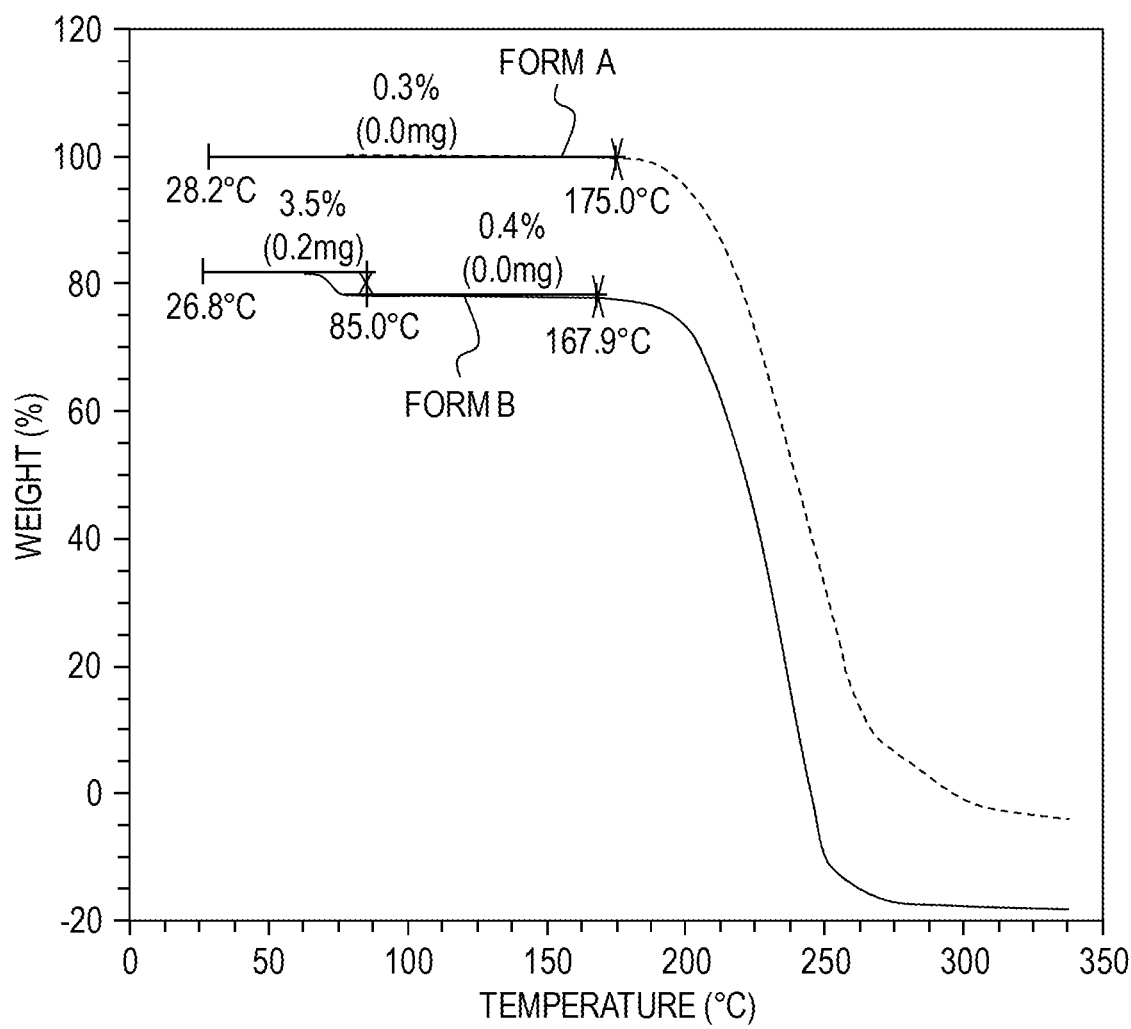
FIG. 4 shows a comparison of the thermogravimetric (TG) thermograms of Forms A and B of APC.

The XRPD pattern of Form B is shown in FIG. 1. The differential scanning calorimetry (DSC) thermogram of Form B exhibited a broad endotherm at 69.1° C. (onset), 71.7° C. (peak max) (FIG. 2). The endotherm is associated with a corresponding weight loss of 3.5% on the TG thermogram, which calculates to approximately 0.5 moles of water. These events are likely due to dehydration. A sharp endotherm is observed at 182.5° C. (onset), 183.6° C. (peak max) followed by an exotherm at 185.2° C. (peak max) possibly due to a recrystallization event. This was followed by an endotherm at 190.1° C. (peak max). DSC and thermogravimetry (TG) thermogram comparisons of Form B and Form A are shown in FIG. 3 and FIG. 4.

Karl Fischer analysis indicated Form B contained ~3.71 wt % water or approximately 0.5 moles. This data was consistent with the weight loss observed in the TG thermogram.

Microscopy images were taken of Form B and showed elongated plates (~50-100 μm) and smaller fragments.

The aqueous solubility of Form B was measured at over 700 mg/ml in different pH buffers as shown in Table 1.

TABLE 1

| Solvent | pH (buffer) measured starting conditions | pH (buffered sample) | Solubility (mg/ml) mean of triplicates |
|---|---|---|---|
| Buffer solution pH 1.2 | 1.2 | 4.5 | 732.26 |
| Buffer solution pH 4.5 | 4.5 | 5.7 | 733.04 |
| Buffer solution pH 5.5 | 5.5 | 6.0 | 741.79 |
| Buffer solution pH 7.4 | 7.4 | 6.4 | 746.41 |

Crystals of APC were submitted for single crystal structure analysis. The structure was determined by single crystal X-ray diffraction. The monoclinic cell parameters and calculated volume are: a=15.9491(8) Å; b=5.8431(6) Å; c=12.7663(12) Å; β=94.404(5)° (α=γ=90°); V=1186.21(18) Å$^3$. The formula weight of the asymmetric unit in the crystal structure of APC Form B is 239.70 g mol$^{-1}$ with Z=4, resulting in a calculated density of 1.342 g cm$^{-3}$. The space group was determined to be C2 (no. 5). The space group and unit cell parameters are in agreement with those obtained previously from XRPD indexing for Form B.

When adequate relative RH is achieved Form A converts to Form B. Interconversion slurry experiments conducted with Form A and Form B suggest that Form B is the more stable form at approximately 50% RH or greater at room temperature.

Slurry experiments were performed with various water activities starting with Form A only and also by conducting interconversion slurries or pre-saturating solutions with APC and then adding equal amounts of Form A and Form B. When slurrying Form A only, conversion to Form B at room temperature occurred at 67% RH, and 40% RH at 2-8° C. With the interconversion slurries, Form B was isolated from all experiments with relative humidities ranging from 50% to 70%.

Figure 5:
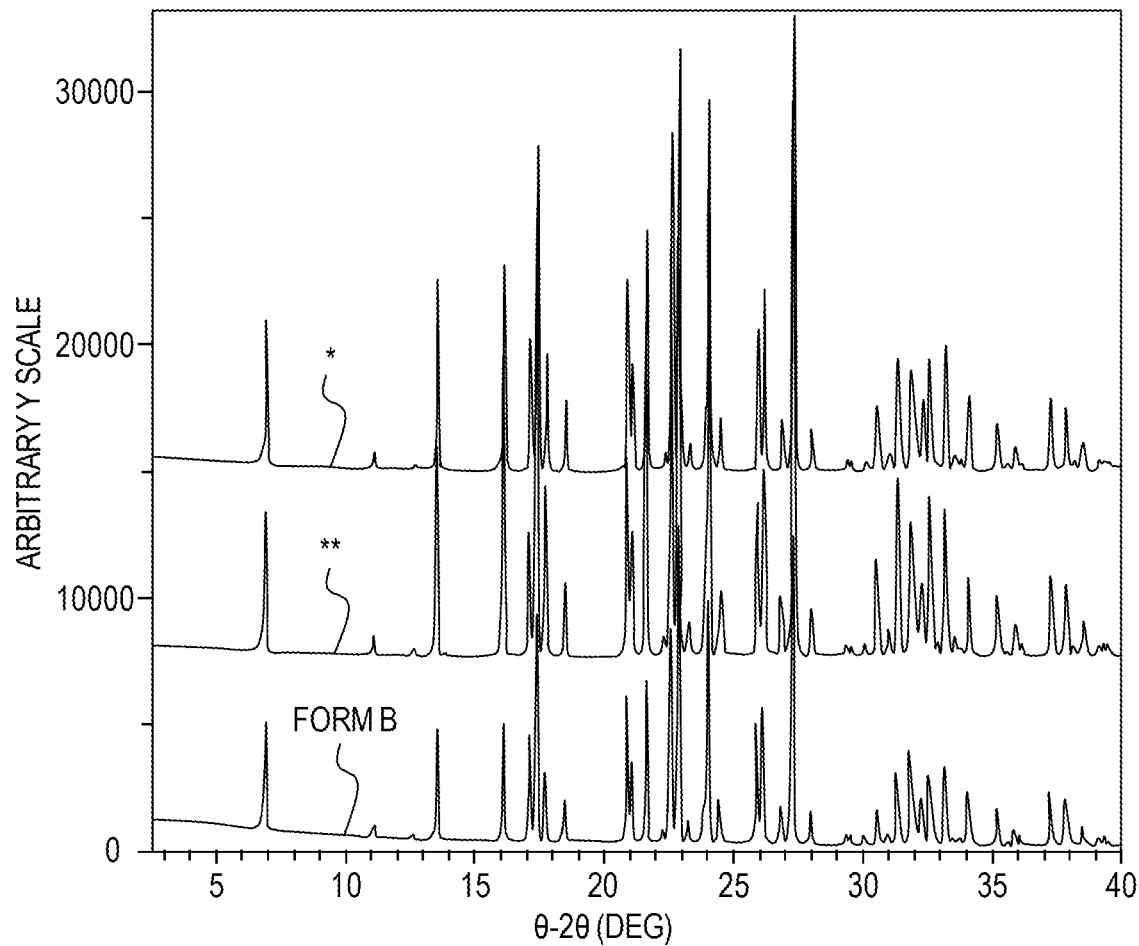
FIG. 5 shows XRPD patterns of the conversion of Form A to Form B of APC.

Two small scale experiments were conducted in acetonitrile:water (95%:5% v:v) to evaluate whether an overnight conversion of Form A to Form B was possible. Experiments were conducted at approximately 98 mg/ml and approximately 51 mg/ml. Both experiments resulted in Form B after slurrying for approximately 24 hours indicating that kinetics of conversion of Form A to Form B can occur within 24 hours (FIG. 5).

Drying studies were performed on Form B. The drying experiments were performed under various temperatures with and without vacuum. Additionally, milling, storage under desiccant, and low RH stressing were conducted. In all experiments, Form B partially or fully dehydrated to Form A. Partial conversion to Form A occurred after vacuum drying at ambient temperature for 1 day, heating at 40° C. for 1 day, storage under desiccant for 1 day, and stressing at 33% RH for 2 weeks. Full dehydration to Form A occurred after vacuum drying at 50° C. for 1 day, heating at 80° C. for 1 day, and milling. The results of the drying studies of Form B suggest that Form B is not stable under low RH or at elevated temperature.

A scaled-up method for producing Form B was developed. APC was slurried in acetonitrile:water (95%:5% v:v) while maintaining the temperature at 22° C. Subsamples of the slurry were taken periodically, vacuum filtered, and analyzed by XRPD. It was found that mixtures of Form B with trace amounts of Form A were observed from approximately 20 to 28.5 hours. Compared to the subsample taken at 20 hours, an increase in Form A was observed in the subsample taken at 24 hours. This may be due to dehydration caused by vacuum filtration and low atmospheric humidity. The slurry was stirred for an additional 3 days and another subsample was taken. XRPD analysis indicated that a subsample taken at approximately 91 hours was Form B. The slurry was isolated by vacuum filtration after slurrying of approximately 121.5 hours, and the wet cake was washed with two filter cake volumes of acetonitrile:water (95%:5% v:v). XRPD analysis indicated the wet cake was composed of Form B. The wet cake was dried under vacuum at ambient temperature for approximately 16 hours. XRPD analysis indicated the dried material dehydrated slightly to Form A, with approximately 5% Form A in the mixture. The dehydration may be avoided by drying without vacuum or drying under high RH (approximately 75%).

The mixture of Form B with a trace amount of Form A was additionally characterized by Karl Fischer for water content determination and solution $^1$H NMR for an estimation of solvent convent. Karl Fischer analysis indicated the mixture contained approximately 3.52% water or 0.47 moles of water per mole of APC. The $^1$H NMR spectrum was consistent with the structure of APC. Water and a trace amount of acetonitrile (0.003 moles per mole of APC) were also observed in the spectrum.

An additional scaled-up method for producing Form B was developed that reduced reaction time and volume and increased yield. Isolation of Form B from Form A was carried out in 5 volumes of solvent (acetonitrile:water (95%: 5% v:v)) at about 20° C. for about 1-2 hours. The drying process was carried out at an oven temperature of 20-25° C. and low vacuum (700-750 mbar). Under these drying conditions Form B was stable and no detectable Form A was formed. This method was used on a 4.5 kg batch of APC and produced Form B with a yield of 93.7%.

Example 2

Synthesis of (R)-2-amino-3-phenylpropyl carbamate hydrochloride with Minimal 2-chloropropane Initially, large scale preparation of APC hydrochloride from the free base was carried out as follows. APC free base solution in isopropyl alcohol was diluted with isopropyl alcohol to a final concentration of 19% w/w. Water (37 g/mol) was added, and the solution was heated to 70° C. Gaseous HCl (about 2 equivalents) was added in the headspace above the solution through a flow meter. As HCl dissolved the temperature increased to 75-80° C. The clear supersaturated solution was seeded quickly within the 15 minutes following the addition. APC hydrochloride crystallized. The suspension was stirred at 78° C., then cooled to 40° C. in 10 hours. The suspension was further cooled to 20° C., then to 3° C. in 2 hours, and stirred at this temperature for 1 hour. The solid was recovered by filtration and washed with isopropyl alcohol. The wet cake was dried under reduced pressure for at least 16 hours.

This method produced unacceptable levels of the potential genotoxic impurity 2-chloropropane (2-CP), which is preferentially at a level of no more than 5 ppm. The levels were likely due to the harsh crystallization conditions (HCl charging close to the boiling point of the reaction mixture, stirring 1 hour at 78° C., then cooling to 40° C. in 10 hours, then progressively cooling to 3° C.). Drying the crystals, even at elevated temperatures, did not reduce the amount of 2-CP. Reslurrying the crystals also was ineffective.

Given the difficulty of removing 2-CP once it was formed, it was necessary to revise the crystallization conditions to avoid the formation of 2-CP. Starting with APC free base in isopropyl acetate prevented formation of 2-CP but the crystallization was poorly controlled, resulting in the formation of a thick crust in the reactor, and produced very small crystals, so the conditions were not suitable. Charging the HCl gas at a lower temperature (30-35° C.) controlled formation of 2-CP but the crystallization was poorly controlled, resulting in the formation of a thick crust in the reactor, and produced a less crystalline material, so the conditions were not suitable.

Because the charging of HCl in gas form caused unwanted spontaneous crystallization in the conditions evaluated, adding HCl in the form of a 37% aqueous solution was tested. This protocol increases the total amount of water 1.76-fold from 37 g/mol to 65 g/mol so the resulting suspension has to be cooled to a lower temperature to maximize the yield. However, the larger amount of water combined with the lower molar excess of acid (1.05 molar equivalents compared to 2 molar equivalents) and the lower temperature contributes to minimizing the rate of formation of 2-CP.

The following general protocol was developed. APC free base solution in isopropyl alcohol was diluted with isopropyl alcohol to a final concentration of 19% w/w. The clear solution was warmed up to 25° C. (20-30° C.). 37% aqueous HCl was slowly added to the clear solution. The temperature was allowed to rise to 30° C. Seeding was applied soon afterwards (within 15 minute). The clear solution was stirred for 15 minutes at 30° C., whereby APC hydrochloride slowly started crystallizing. 37% aqueous HCl was further added to the suspension. The mixture was stirred at 30° C. for 1 hour, then cooled to −15° C. in 2 hours, and stirred at this temperature for 1 hour. The product was recovered as a white crystalline solid and washed with isopropyl alcohol. The wet product was dried at 35° C. (30-40° C.) under a nitrogen stream.

In one example, a solution of APC free base 16.9 g, 0.0871 mol) was diluted with isopropyl alcohol (43.8 g) and warmed to 30° C. 37% aqueous HCl (4.51. g, 0.0458 mol, 0.525. mol equiv) was added dropwise, keeping the temperature ≤35° C. APC hydrochloride (22 mg) was added to the clear solution. The solution became turbid almost immediately. After 15 minutes a suspension was obtained. No crystallization around the reactor walls occurred. Further 37% aqueous HCl (4.51 g, 0.0458 mol, 0.525. mol equiv) was added dropwise, keeping the temperature ≤35° C. After charging the suspension was stirred at 30° C. for 1 hour, cooled to −15° C. in 2 hours and stirred 2 hours at this temperature. The product was recovered by filtration, washed with IPA (16.7 g) and dried at 35° C., 30-50 mbar for 17 hours under air flow. 16.87 g product was recovered (yield 83.96%). The crystallization occurred very smoothly. The product was a white crystalline powder. No 2-CP was detected.

Two additional batches were prepared using the same protocol. In both batches 2-CP levels in the product were less than 1 ppm.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A composition comprising (R)-2-amino-3-phenylpropyl carbamate hydrochloride and 2-chloropropane, wherein the composition comprises less than about 5 ppm 2-chloropropane.

2. The composition of claim 1, wherein the composition comprises less than about 1 ppm 2-chloropropane.

3. The composition of claim 1, wherein the composition is a dosage form.

4. The composition of claim 3, wherein the composition is an immediate release oral dosage form.

5. The composition of claim 4, wherein the composition is a tablet or a capsule.

6. A method of treating narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity in a subject in need thereof, or promoting smoking cessation in a subject in need thereof, comprising administering to the subject the composition of claim 1.

7. The method of claim 6, wherein the composition is administered once per day.

8. The method of claim 6, wherein the composition is administered more than once per day.

* * * * *

UNITED STATES PATENT AND TRADEMARK OFFICE
CERTIFICATE OF CORRECTION

PATENT NO. : 11,560,354 B2
APPLICATION NO. : 17/091222
DATED : January 24, 2023
INVENTOR(S) : Fionn Hurley It is certified that error appears in the above-identified patent and that said Letters Patent is hereby corrected as shown below:

In the Specification

Column 3, Line 28: Please correct "10%" to read --+10%--

Column 3, Line 29: Please correct "5%" to read --+5%--

Signed and Sealed this
Ninth Day of May, 2023

Katherine Kelly Vidal
*Director of the United States Patent and Trademark Office*